United States Patent
Schweizer et al.

(10) Patent No.: US 12,032,192 B2
(45) Date of Patent: Jul. 9, 2024

(54) REFRACTIVE INDEX CALCULATIONS FOR MATERIALS

(71) Applicant: Dassault Systemes Americas Corp., Waltham, MA (US)

(72) Inventors: Sabine Schweizer, Angelbachtal (DE); Kwan Skinner, Mesa, AZ (US); Lalitha Subramanian, Newtown, PA (US)

(73) Assignee: Dassault Systemes Americas Corp., Waltham, MA (US)

( * ) Notice: Subject to any disclaimer, the term of this patent is extended or adjusted under 35 U.S.C. 154(b) by 212 days.

(21) Appl. No.: 17/818,469

(22) Filed: Aug. 9, 2022

(65) Prior Publication Data

US 2024/0053524 A1 Feb. 15, 2024

(51) Int. Cl.
  *G02B 5/30* (2006.01)
  *G01N 21/21* (2006.01)
  *G01N 21/23* (2006.01)

(52) U.S. Cl.
  CPC ........... *G02B 5/3083* (2013.01); *G01N 21/21* (2013.01); *G01N 21/23* (2013.01); *G02B 5/305* (2013.01)

(58) Field of Classification Search
  CPC ...... G02B 5/3083; G02B 5/305; G01N 21/21; G01N 21/23; G16C 20/30; G16C 20/70; G16C 60/00; G06F 30/20; G06F 2119/08; G06F 2119/14
  USPC ....................................................... 356/365
  See application file for complete search history.

(56) References Cited

U.S. PATENT DOCUMENTS

| | | | |
|---|---|---|---|
| 2002/0075445 A1* | 6/2002 | Dabrowski | G02F 1/1416 349/174 |
| 2006/0215159 A1* | 9/2006 | Smith | G01N 21/23 356/367 |

FOREIGN PATENT DOCUMENTS

| | | |
|---|---|---|
| CN | 114300070 A | 4/2022 |
| JP | 2011-060275 A | 3/2011 |

OTHER PUBLICATIONS

Simpson, S.H, et al. "Calculation of the birefringences of nematic liquid crystals at optical and infrared wavelengths", J. Chem. Phys. 123, 134904 (2005).

(Continued)

*Primary Examiner* — Md M Rahman
(74) *Attorney, Agent, or Firm* — Hamilton, Brook, Smith & Reynolds, P.C.

(57) ABSTRACT

Embodiments calculate birefringence of materials. One such embodiment builds one or more three-dimensional structure models of one or more compounds forming a material. Each built three-dimensional structure model is aligned along a molecular axis and one or more tilt angles are set for each aligned three-dimensional structure model. A molecular polarizability tensor for each three-dimensional structure model with the set tilt angles is then calculated. An embodiment accounts for anisotropy by measuring the width and length of each model with the set tilt angles to determine aspect ratios. To continue, birefringence of the material is calculated based on the determined molecular polarizability tensors of the one or more models. Embodiments can be employed for simulating, optimizing, and designing real-world objects, e.g., in an optimization to select a material for a phone display that conforms with performance/manufacturing requirements.

22 Claims, 6 Drawing Sheets

(56) References Cited

OTHER PUBLICATIONS

Andrienko, D., "Introduction to liquid crystals", Journal of Molecular Liquids, vol. 267, Feb. 3, 2018, pp. 520-541.
Chen, Z., et al., "Calculation on frequency and temperature properties of birefringence of nematic liquid crystal 5CB in terahertz band", Chemical Physics Letters, vol. 645, Feb. 2016, pp. 205-209.
Dabrowski, R., et al., "High Birefringence Liquid Crystals", Crystals, vol. 3, No. 3, 2013, pp. 443-482.
Rerat, M., et al., "From anisotropy of dielectric tensors to birefringence: a quantum mechanics approach", Rendiconti Lincei. Scienze Fisiche e Naturali, vol. 31, 2020, pp. 835-851.
Terui, Y., et al., "Coefficients of molecular packing and intrinsic birefringence of aromatic polyimides estimated using refractive indices and molecular polarizabilities", Journal of Polymer Science Part B, vol. 42, No. 12, May 6, 2004, pp. 2354-2366.
Wang, J., et al., "Theoretical study and enhancement of the birefringence of fluorinated poly(methacrylate)", Colloid and Polymer Science, vol. 295, 2017, pp. 237-246.

* cited by examiner

REFRACTIVE INDEX CALCULATIONS FOR MATERIALS

BACKGROUND

Calculation of refractive properties, e.g., birefringence, of materials from scratch is typically applied to pure compounds. Usually, an "order parameter" is used and the molecular anisotropy has to be taken into account for such calculations. The value of the order parameter is typically a guess provided by an experienced person or, at best, determined from experimental results. However, experimental results providing the order parameter are only available for a limited number of pure compounds.

SUMMARY

Therefore, reliable, first principles based functionality is needed to estimate the order parameter and the molecular anisotropy. One such embodiment provides this functionality by (i) building three-dimensional structures of compound(s), (ii) constructing a nematic phase structure, (iii) performing molecular dynamics simulations to equilibrate the constructed nematic phase structure, (iv) analyzing structure of the nematic phase, e.g., angles between individual molecules and room axis, and (v) determining the order parameter from the angles.

In addition, functionality is needed that screens pure compounds and mixtures for their birefringent properties. Embodiments provide such functionality. An example embodiment is directed to a method for a priori materials screening from first principles simulation techniques where there is an absence of experimental data.

Embodiments can be employed for three-dimensional (3D) atomistic modeling and simulation of materials, e.g., liquid crystal materials, in the absence of experimental data. Embodiments are applicable to pure compounds or mixtures of organic molecules forming an ordered structure, amongst other examples. Further, embodiments can automatically predict refractive indices so as to design materials for optical displays (e.g., displays for phones, computers, television screens, flat panels, and other electronic devices), filters, smart films/coatings, and lenses, amongst other examples. As such, embodiments enable an efficient way for designing such products.

Embodiments can be used to examine organic molecules. Additionally, embodiments can determine refractive properties of polymeric systems through extrapolation from monomeric and oligomeric molecules to polymeric systems using, amongst other examples, correlative or machine learning-based methods.

An embodiment is directed to a computational method for calculating the birefringence of a material, e.g., a liquid crystal mixture. In an embodiment, for each pure component, tilted structures of different conformers of the molecule(s) are generated. For each of these structures, the polarizability is calculated and based on the calculated polarizability, the birefringence is determined. For each compound, an average, e.g., weighted average, of the ordinary and extraordinary refractive indices for the different conformations and orientations is calculated. In an embodiment, the ordinary and extraordinary indices for compounds of a mixture are weighted according to the composition of the mixture. For determining the tilt angle, an embodiment builds a nematic phase, e.g., using BIOVIA® Materials Studio®. In turn, molecular dynamics simulations are performed and from the resulting trajectory, average tilt angles for each compound are determined. Different conformations can be obtained through a systematic conformer search, from molecular dynamics simulations, or generated manually, amongst other examples.

Another embodiment is directed to a computer-implemented method for calculating birefringence of a material. The method begins by building one or more three-dimensional structure models of one or more compounds that form a material. Then, for each of the built one or more three-dimensional structure models: (i) the three-dimensional structure model is aligned along a molecular axis, (ii) one or more tilt angles for the aligned three-dimensional structure model are set, and (iii) using the aligned three-dimensional structure model with the set one or more tilt angles, a molecular polarizability tensor for the aligned three-dimensional structure model with the set one or more tilt angles is calculated. In turn, birefringence of the material is calculated based on the calculated molecular polarizability tensors.

Embodiments may be used to determine birefringence of varying materials. For instance, in an embodiment, the material (for which the birefringence is determined) is a liquid crystal mixture, an organic molecule-based material, an organic-molecule-based pure compound, or a mixture of organic molecules.

An embodiment builds the one or more three-dimensional structure models of the one or more compounds by first building one or more initial three-dimensional structure models of the one or more compounds forming the material. Such an embodiment then performs, based on the built one or more initial three-dimensional structure models, a conformational search to generate a respective set of three-dimensional structure models of conformers for each of the one or more compounds. In turn, for each generated set of three-dimensional structure models of conformers, a subset of conformers is selected from the generated set of three-dimensional structure models of conformers. Such an embodiment sets (i) the one or more initial three-dimensional structure models and (ii) three-dimensional structure models of conformers corresponding to each selected subset of conformers, as the built one or more three-dimensional structure models of the one or more compounds forming the material. In one such embodiment, selecting a subset of conformers comprises selecting a low-energy conformer, a medium-energy conformer, and a high-energy conformer. Further, in yet another embodiment, performing a conformational search comprises at least one of: (i) performing a systematic conformational search, (ii) performing a molecular dynamics simulation for conformational sampling, and (iii) receiving user input selecting one or more desired conformers.

An embodiment performs the aforementioned molecular dynamics simulation for conformational sampling by first building a three-dimensional bulk structure model of the material and, second, performing a molecular dynamics simulation at one or more temperatures using the built three-dimensional bulk structure model. Performing the molecular dynamics simulation creates a trajectory. From the trajectory, individual molecules of the one or more compounds are selected from the three-dimensional bulk structure model. In turn, a respective energy of each individual molecule selected is calculated based on a geometry optimization of the individual molecules selected. The determined respective energy of each individual molecule is statistically analyzed to define an energy range for each of the one or more compounds and each defined energy range of the one or more compounds is split into sub-range bins. Each conformer in each respective set of three-dimensional structure models of conformers of the one or more compounds is assigned to a given energy bin of the sub-range bins. The number of conformers in each sub-range bin is determined and, based on the determined number of conformers in each sub-range bin, each selected subset of conformers is identified. Further, such an embodiment can weight importance of each conformer in each selected subset of conformers.

According to an embodiment, setting the one or more tilt angles comprises at least one of systematically varying the one or more tilt angles and automatically determining the one or more tilt angles from a molecular dynamics simulation. In another embodiment, setting one or more tilt angles for the aligned three-dimensional structure model comprises building a nematic phase structure of the material formed of the one or more compounds and geometrically optimizing the built nematic phase structure. In turn, molecular dynamics simulations of the geometrically optimized nematic phase structure equilibrated at one or more temperatures are performed. In such an embodiment, the one or more tilt angles, between a molecule axis and room axis for each molecule, are determined by analyzing results of performing the molecular dynamics simulations of the geometrically optimized nematic phase structure equilibrated at the one or more temperatures. In one such embodiment, the one or more tilt angles are determined by statistically analyzing the determined one or more tilt angles to select a subset of tilt angles. According to an embodiment, statistically analyzing the determined one or more tilt angles comprises at least one of (i) generating a tilt angle distribution for each compound contained in the nematic phase structure, (ii) averaging each tilt angle distribution over time of the molecular dynamics simulations, and (iii) deriving weighting factors for the tilt angles, if more than one tilt angle is applied.

In yet another embodiment, calculating a molecular polarizability tensor using the aligned three-dimensional structure model with the set one or more tilt angles comprises at least one of: performing geometry optimization of the aligned three-dimensional structure model with the set one or more tilt angles and performing vibrational frequency analysis to confirm local minimum geometry of the aligned three-dimensional structure model with the set one or more tilt angles.

In calculating birefringence of the material based on the calculated molecular polarizability tensors, an embodiment, for each calculated molecular polarizability tensor, selects relevant components from the calculated molecular polarizability tensor and calculates an ordinary refractive index and an extraordinary refractive index using the selected relevant components. In turn, the birefringence of the material is calculated using the ordinary refractive index and the extraordinary refractive index calculated for each calculated molecular polarizability tensor.

Various operations may be involved in calculating the birefringence using the ordinary refractive index and the extraordinary refractive index calculated for each calculated molecular polarizability tensor. For instance, an embodiment calculates the birefringence for a conformation of the one or more compounds and one tilt angle of the set one or more tilt angles. In another embodiment, where the one or more tilt angles comprises a plurality of tilt angles, the birefringence is calculated for (i) a conformation of the one or more compounds and the plurality of tilt angles or (ii) multiple conformations of the one or more compounds and a given tilt angle of the plurality of tilt angles, or (iii) a plurality of conformations of the one or more compounds and the plurality of tilt angles. According to yet another embodiment, as part of calculating the birefringence, the ordinary refractive index and the extraordinary refractive index calculated for each calculated molecular polarizability tensor are averaged. Yet another embodiment weights contributions of each ordinary refractive index and each extraordinary refractive index calculated.

An embodiment determines a respective aspect ratio for each of the built one or more three-dimensional structure models and, for each calculated molecular polarizability tensor, calculates the ordinary refractive index and the extraordinary refractive index using the selected relevant components and the determined respective aspect ratio.

Another embodiment of the method calculates the density of the material. One such embodiment calculates the density of the material by performing molecular dynamics simulations for the material to determine a trajectory and analyzing the trajectory and/or performing a machine learning-based analysis to predict the density of the material.

Embodiments may perform additional analysis and real-world actions using the determined birefringence. For instance, an embodiment simulates the material using the determined birefringence. Amongst other examples, the simulation may determine behavior of the material in real-world use cases. Based on the simulation (and results thereof), another embodiment determines a design for a real-world object that uses the material. According to an embodiment, the real-world object is an optical display, filter, film, coating, or lens, amongst other examples. Another embodiment iterates the building, aligning, setting, calculating a molecular polarizability tensor, calculating birefringence, and simulating for each of a plurality of candidate materials. Then, based on results of the simulating, such an embodiment selects a given material from among the candidate materials.

Yet another embodiment is directed to a system that calculates birefringence of a material. The system includes a processor and a memory with computer code instructions stored thereon. In such an embodiment, the processor and the memory, with the computer code instructions, are configured to cause the system to implement any embodiments or combination of embodiments described herein.

Another embodiment is directed to a cloud computing implementation for calculating birefringence of a material. Such an embodiment is directed to a computer program product executed by a server in communication across a network with one or more clients, where the computer program product comprises instructions which, when executed by one or more processors, causes the one or more processors to implement any embodiments or combination of embodiments described herein.

It is noted that embodiments of the method, system, and computer program product may be configured to implement any embodiments, or combination of embodiments, described herein.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

Embodiments calculate birefringence of materials, e.g., organic materials, liquid crystal materials, etc. Embodiments apply to both pure compounds and mixtures of compounds.

Birefringence is the difference between the extraordinary and ordinary refractive index of a material. The extraordinary and ordinary index can be calculated based on the molecular polarizability tensor, which can be calculated using, amongst other examples, density functional theory calculations. Different approaches exist to relate the molecular polarizability tensor with the refractive indices. For example, the Lorentz-Lorenz equation and extensions of the Clausius-Mossotti equation, such as the Neugebauer-Bordewijk-de Jeu (NBJ) equation (see, e.g. J. Chem. Phys. 123, 134904, 2005) relate the polarizability with the refractive indices.

Spatial orientation and extension of the compound affect the refractive index. It is therefore crucial to be able to determine the molecular orientation and extension of the material. Embodiments derive both properties from first principles. According to an embodiment, these two properties take the ordering of the nematic phase and the anisotropy into account.

Figure 1:
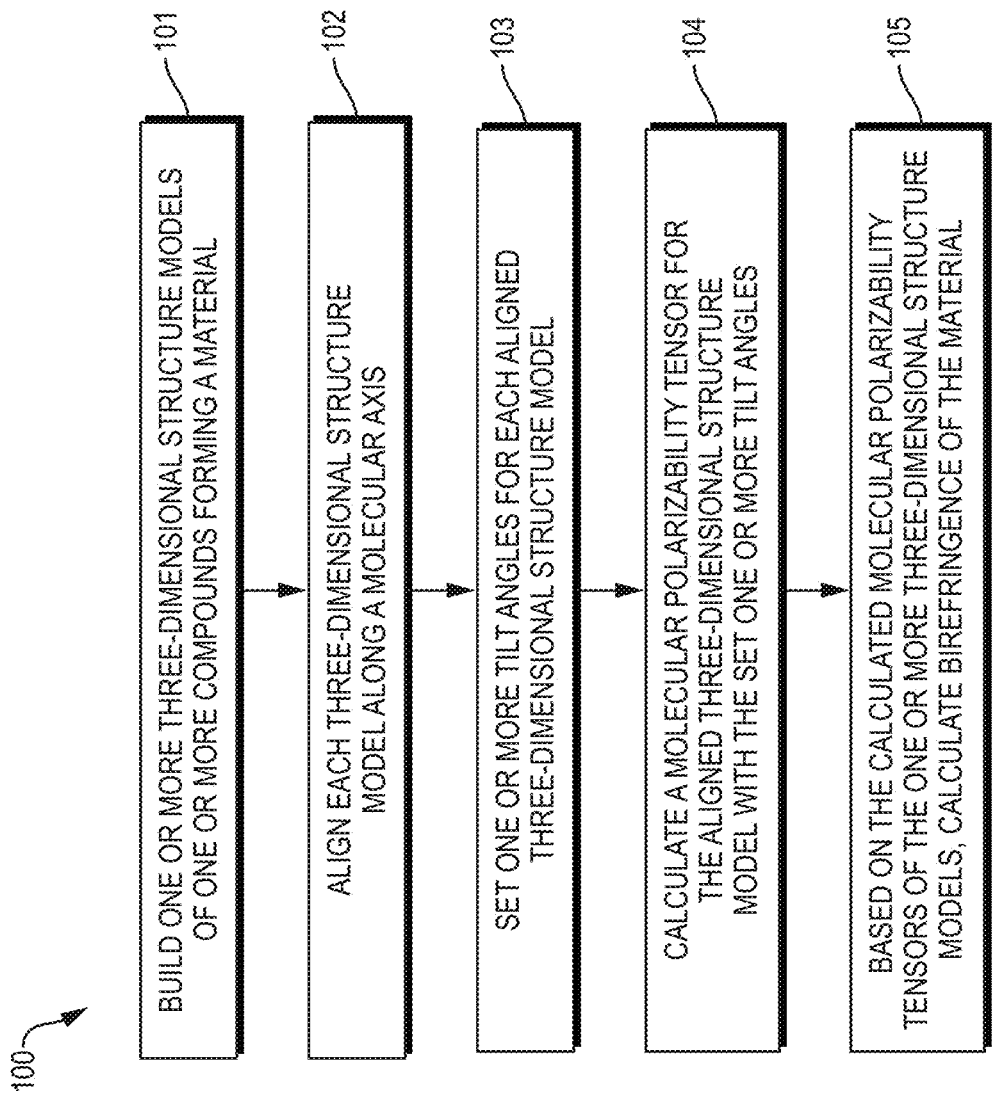
FIG. 1 is a flowchart of a method for determining birefringence of a material according to an embodiment.

FIG. 1 illustrates one such example method embodiment 100. The method 100 is a computer-implemented method for calculating the birefringence of a material. The method 100 begins at step 101 by building, e.g., in computer memory, one or more three-dimensional structure models of one or more compounds that form a material. According to an embodiment, the method 100 builds the models at step 101 in a way that accounts for molecular anisotropy by performing conformational sampling and considering different conformations. To continue, for each of the built one or more three-dimensional structure models, the method 100 (i) aligns the three-dimensional structure model along a molecular axis (step 102), (ii) sets one or more tilt angles for the aligned three-dimensional structure model (step 103), and (iii) using the aligned three-dimensional structure model with the set one or more tilt angles, calculates a molecular polarizability tensor for the aligned three-dimensional structure model with the set one or more tilt angles (step 104). In turn, at step 105, birefringence of the material is calculated based on the calculated molecular polarizability tensors.

To illustrate, consider a simplified example, where the material is formed of two compounds, A and B. At step 101 a three-dimensional structure model of A (referred to as "A") and a three-dimensional structure model of B (referred to as "B") are built and held in working computer memory. Conformations of A and B may also be built at step 101 as described herein, but in this simplified illustrative example, conformational sampling/consideration is not carried out. At step 102, the model A is aligned along a molecular axis to form the aligned model A' and the model B is aligned along a molecular axis to form the aligned model B'. Next, at step 103, tilt angles of the model A' and B' are set, resulting in the models A" and B". It is noted that in embodiments, multiple tilt angles are utilized and models with the multiple tilt angles are used and weighted as described herein. To continue, the models A" and B" are then used at step 104 to calculate a molecular polarizability tensor of model A" and a molecular polarizability tensor of model B". The polarizability tensors are used at step 105 to calculate (e.g., using a weighted average of the polarizability tensors or ordinary and extraordinary refractive indices, based on amounts of A and B in the material) and output an indication of the birefringence of the material.

As noted, the method 100 is computer implemented and, as such, the functionality and effective operations, e.g., the building (101), aligning (102), setting (103), calculating molecular polarizability tensors (104), and calculating birefringence (105), are automatically implemented by one or more digital processors. Moreover, the method 100 can be implemented using any computer device or combination of computing devices known in the art. Amongst other examples, the method 100 can be implemented using the computer system 550 described hereinbelow in relation to FIG. 5 and the computer network environment 660 described hereinbelow in relation to FIG. 6.

The method 100 may determine birefringence of varying materials, e.g., mixtures of compounds and molecules. In an embodiment of the method 100, the material (for which the birefringence is determined at step 105) is a liquid crystal mixture, an organic molecule-based material, an organic-molecule-based pure compound, or a mixture of organic molecules.

In an embodiment of the method 100, building the one or more three-dimensional structure models of the one or more compounds at step 101 includes first, building one or more initial three-dimensional structure models of the one or more compounds forming the material. Amongst other examples, embodiments build the one or more models at step 101 using known software platforms, e.g., BIOVIA® Materials Studio®, that provide 3D viewer and building functionalities for generating 3D molecular structures. After building the initial models, such an embodiment then performs, based on the built one or more initial three-dimensional structure models in computer memory, a conformational search to generate a respective set of three-dimensional structure models of conformers for each of the one or more compounds. In turn, for each generated set of three-dimensional structure models of conformers, a subset of conformers is selected from the generated set of three-dimensional structure models of conformers. Finally, such an embodiment sets (i) the one or more initial three-dimensional structure models and (ii) three-dimensional structure models of conformers corresponding to each selected subset of conformers, as the built one or more three-dimensional structure models of the one or more compounds forming the material.

To illustrate the foregoing embodiment, consider an example where compounds C and D form the material. Such an example embodiment first builds initial models C and D in working memory. The models C and D are then used to perform a conformational search, which yields the sets of conformers for compounds C and D, [C1, C2, C3] and [D1, D2, D3], respectively. From the foregoing sets, subset of conformers are selected, in this example C2 and C3 are selected from the set of conformers for compound C, and D2 and D3 are selected from the subset of conformers for compound D. The selected conformers, C2, C3, D2, and D3, and optionally the initial models C and D, are then set as the built three-dimensional structure models. In this way, such an embodiment, at step 101, builds models of the compounds, and conformers of the compounds, that form the material. As such, in this example embodiment, it is these models C, C2, C3, D, D2, and D3, that are then used in the other steps, e.g., 102, 103, and 104 of the method 100. In such an embodiment, each model C, C2, C3, D, D2, and D3 is aligned (step 102) and has tilt angles set (step 103) and, then, a molecular polarizability tensor is calculated (step 104) for each aligned tilt angle set model of C, C2, C3, D, D2, and D3. From the polarizability tensors, the diagonal elements are used to calculate the ordinary and extraordinary refractive index for each aligned tilt angle set model of C, C2, C3, D, D2, and D3. The calculated ordinary refractive indices and the extraordinary refractive indices are averaged compound-wise separately, i.e. the average (Av_OR_C average ordinary refractive index of the set C) of the ordinary indices of C, C2, C3 is calculated, the average (Av_ER_C average extraordinary refractive index of the set C) of the extraordinary indices of C, C2, C3 and the same for the set D, D2, D3, i.e. average Av_OR_D average ordinary refractive index of the set D and average Av_ER_D average extraordinary refractive index of the set D. The contributions of the individual conformations (C, C2, C3 and D, D2, D3) may be weighted. The average values of the ordinary refractive indices Av_OR_C and Av_OR_D are averaged and/or weighted according to the composition of the mixture to obtain Av_OR_mix. The same is done with the average values Av_ER_C and Av_ER_D to obtain Av_ER_mix. The birefringence is then the difference between Av_OR_mix and Av_ER_mix.

In an embodiment of the method 100, where conformational searching is performed and subsets of conformers are selected at step 101, selecting a subset of conformers comprises selecting a low-energy conformer, a medium-energy conformer, and a high-energy conformer. Further, in yet another embodiment, performing a conformational search comprises at least one of: (i) performing a systematic conformational search, (ii) performing a molecular dynamics simulation for conformational sampling, and (iii) receiving user input selecting one or more desired conformers. In an embodiment, the systematic conformational searching and molecular dynamics simulation for conformational sampling may be performed using techniques known to those of skill in the art. An embodiment of the method 100 performs the molecular dynamics simulation for conformational sampling by first, building a three-dimensional bulk structure model of the material. Second, a molecular dynamics simulation is performed at one or more temperatures using the built three-dimensional bulk structure model. Performing the molecular dynamics simulation creates a trajectory of the bulk structure, i.e., coordinates of the molecular system in space as a function of time. From the trajectory, individual molecules of the one or more compounds are selected. In turn, a respective energy of each individual molecule selected is calculated based on a geometry optimization of the individual molecules selected. The determined respective energies of each individual molecule are statistically analyzed to define an energy range for each of the one or more compounds and each defined energy range of the one or more compounds is split into sub-range bins. In this way, such an embodiment analyzes the conformers of each compound based on each compound's individual energy. Each conformer in each respective set of three-dimensional structure models of conformers of the one or more compounds is assigned to a given energy bin of the sub-range bins. The number of conformers in each sub-range bin is determined and, based on the determined number of conformers in each sub-range bin, each selected subset of conformers is identified. For instance, in an embodiment the number of conformers in each sub-range bin can be used for importance weighting, e.g., if there are many conformers in a bin, this conformation is important and selected. If there are sub-range bins with a small number of conformers and other sub-range bins with a large number of conformers, such an embodiment would select conformations from the sub-range bins containing a large number of molecules and drop the others. Further, such an embodiment can weight importance of each conformer in each selected subset of conformers.

As noted above, at step 102, each three-dimensional structure model is aligned 102 along a molecular axis. In an embodiment, each model is consistently aligned at step 102. According to an embodiment, the molecular axis is a principal axis of the moment of inertia of the three-dimensional structure model.

According to an embodiment, setting the one or more tilt angles at step 103 comprises at least one of systematically varying the one or more tilt angles and automatically determining the one or more tilt angles from a molecular dynamics simulation. In an embodiment, the systematic searching may be implemented using a grid scan or Boltzmann technique. Alternatively, random sampling can be used. An example tilt angle 331 is show in FIG. 3 and further described hereinbelow.

Figure 4:
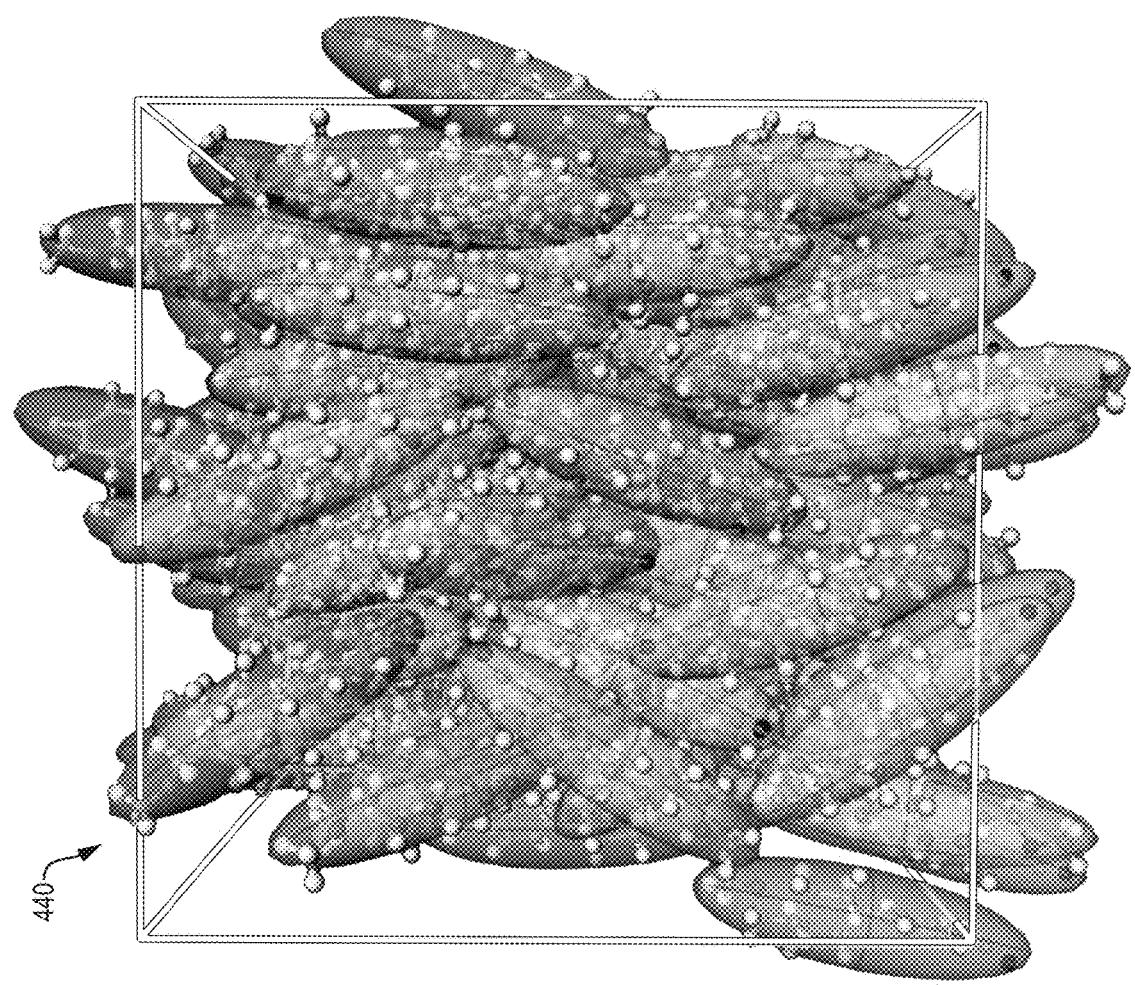
FIG. 4 illustrates a model of a nematic phase of a material that may be used in a molecular dynamics simulation according to an embodiment.

In an embodiment, setting one or more tilt angles at step 103 for the aligned three-dimensional structure model comprises building a nematic phase structure of the material formed of the one or more compounds and geometrically optimizing the built nematic phase structure. An example nematic phase structure model 440 is shown in FIG. 4 and described hereinbelow. In turn, molecular dynamics simulations of the geometrically optimized nematic phase structure are performed at one or more temperatures. In such an embodiment, the one or more tilt angles, between a molecule axis and room axis for each molecule, are determined by analyzing results of performing the molecular dynamics simulations of the geometrically optimized nematic phase structure equilibrated at the one or more temperatures. In one such embodiment, the one or more tilt angles are determined by statistically analyzing the determined one or more tilt angles to select a subset of tilt angles. According to an embodiment, statistically analyzing the determined one or more tilt angles comprises at least one of (i) generating a tilt angle distribution for each compound contained in the nematic phase structure, (ii) averaging each tilt angle distribution over time of the molecular dynamics simulations, and (iii) deriving weighting factors for the tilt angles, if more than one tilt angle is applied.

In an embodiment of the method 100, calculating a molecular polarizability tensor at step 104 using the aligned three-dimensional structure model with the set one or more tilt angles comprises at least one of: performing geometry optimization of the aligned three-dimensional structure model with the set one or more tilt angles and performing vibrational frequency analysis to confirm local minimum geometry of the aligned three-dimensional structure model with the set one or more tilt angles.

In calculating birefringence of the material based on the calculated molecular polarizability tensors at step 105, an embodiment of the method 100, selects, for each calculated molecular polarizability tensor, relevant components from the calculated molecular polarizability tensor and calculates an ordinary refractive index and an extraordinary refractive index using the selected relevant components. According to an embodiment, the relevant components are the diagonal elements of the polarizability tensor. In turn, the birefringence of the material is calculated using the ordinary refractive index and the extraordinary refractive index calculated for each calculated molecular polarizability tensor.

At step 105, various operations may be involved in calculating the birefringence using the ordinary refractive index and the extraordinary refractive index calculated for each molecular polarizability tensor. For instance, an embodiment of the method 100 calculates the birefringence for a conformation of the one or more compounds and one tilt angle of the set one or more tilt angles. One such embodiment calculates the birefringence based on the Lorentz-Lorentz equation or extensions of the Clausius-Mossotti equation, such as the Neugebauer-Bordewijk-de Jeu (NBJ) equation. In another embodiment of the method 100, where the one or more tilt angles comprises a plurality of tilt angles, the birefringence is calculated at step 105 for (i) a conformation of the one or more compounds and the plurality of tilt angles or (ii) multiple conformations of the one or more compounds and a given tilt angle of the plurality of tilt angles, or (iii) a plurality of conformations of the one or more compounds and the plurality of tilt angles. According to yet another embodiment, as part of calculating the birefringence at step 105, the ordinary refractive index and the extraordinary refractive index calculated for each calculated molecular polarizability tensor are averaged. Embodiments can average the indices over different conformations, tilt angles, and/or compounds (in the case of mixtures).

Yet another embodiment weights contributions of each ordinary refractive index and each extraordinary refractive index calculated. In an embodiment, the indices (ordinary refractive and extraordinary refractive) are weighted based on their associated conformations' contributions to the material. Similarly, weighting may be based on each compounds contribution to the material. To illustrate, if a material is made of equal amounts of compound A and compound B (as published, e.g., by a manufacturer), indices for A and B are each weighted at 0.5 and 0.5. If, however, A and a conformer of A, A', each make up one quarter of the material (as estimated using techniques described herein, e.g., statistical analysis of molecular dynamics simulations), the indices for A are given a weight of 0.25 and the indices for A' are given a weight of 0.25.

Figure 2:
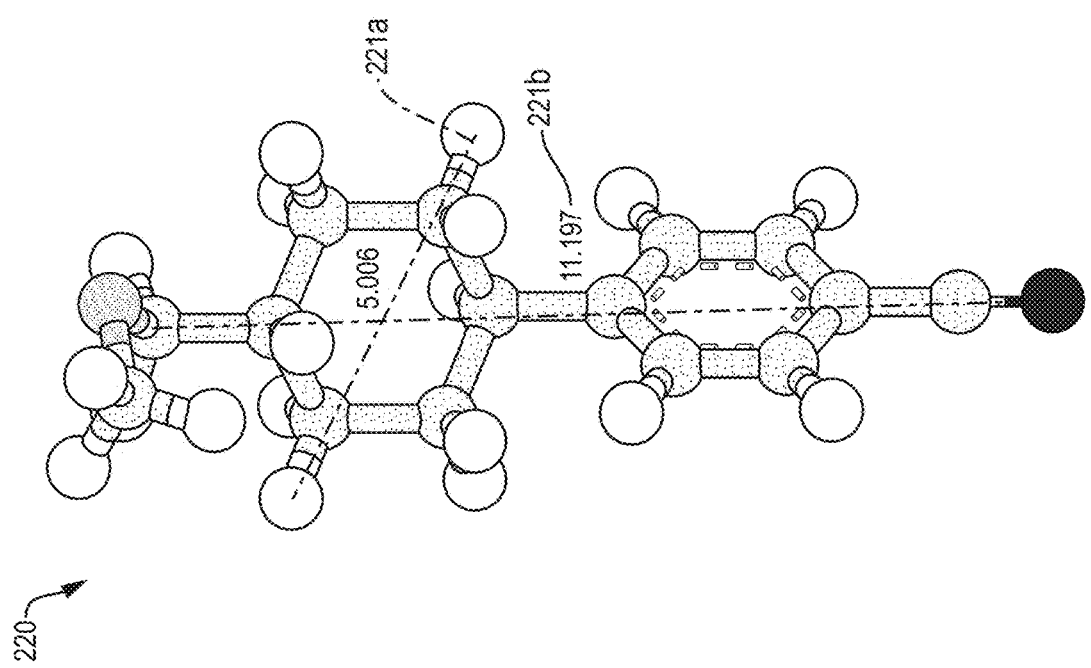
FIG. 2 illustrates measurements for determining aspect ratios according to an embodiment.

An embodiment of the method 100 determines a respective aspect ratio for each of the one or more three-dimensional structure models built at step 101. Example measurements 221a and 221b for determining the aspect ratio are shown in FIG. 2 and described hereinbelow. An embodiment determines the aspect ratios by measuring dimensions of the three-dimensional structure models or rigid core parts of the three-dimensional structure models. The dimensions can be measured between atoms or can be determined from user-defined ellipsoids based on the 3D structure of the respective model. In such an embodiment, for each calculated molecular polarizability tensor, the ordinary refractive index and the extraordinary refractive index are calculated using the selected relevant components and the determined respective aspect ratio. In an embodiment, if the material is anisotropic, the aspect ratios are determined and used in the approach/equations for determining the ordinary refractive index and the extraordinary refractive index. In this way, determining and using the aspect ratio to calculate the birefringence accounts for the molecular anisotropy.

Another embodiment of the method 100 calculates the density of the material. One such embodiment calculates the density of the material by performing molecular dynamics simulations for the material to determine a trajectory and analyzing the trajectory and/or performing a machine learning-based analysis to predict the density of the material. The determined density may also be a temperature dependent density. According to an embodiment, the determined density is used in equations to calculate the refractive indices.

Embodiments of the method 100 may perform additional analyses and real-world actions using and/or based on the determined birefringence. For instance, an embodiment simulates use of the material in a real-world scenario using, amongst other properties, the determined birefringence. Amongst other examples, the simulation may determine behavior of the material in real-world use cases. The simulation may determine, for example, efficiency and operation of the material in a particular use case, e.g., as a phone screen. Based on the simulation (and results thereof), another embodiment determines a design for a real-world object that uses the material. According to an embodiment, the real-world object is an optical display, filter, film, coating, or lens, amongst other examples.

Embodiments of the method 100 may also perform a simulation to determine modifications of the material, e.g., the structure and/or composition of the material. These modifications may be identified by repeating the method 100 for a material with varied properties until a material is identified that meets parameters/requirements. Further, modifications to the material and underlying composition may be virtually tested using embodiments of the method 100.

Another embodiment of the method 100 iterates the building 101, aligning 102, setting 103, calculating a molecular polarizability tensor 104, calculating birefringence 105, and simulating for each of a plurality of candidate materials. Then, based on results of the simulating, such an embodiment selects a given material from among the candidate materials. In this way, such an embodiment may begin with a plurality of candidate materials for a real-world application, e.g., a phone screen, and select a given material from amongst the candidates, based on results of the simulation showing that the selected given material meets requirements.

Embodiments of the method 100 may use file formats/structures of molecule modeling platforms, e.g., BIOVIA® Materials Studio® to store to various models and values determined/used by the method 100, e.g., the three-dimensional models, tilt angles, weights, molecular polarizability tensors, birefringence, and any other data described herein. An embodiment of the method 100 stores tilt angle and molecular axis alignment data in the coordinates of the atomic positions. The atomic coordinates can be stored in different file formats, e.g., using formats available in BIOVIA®. In embodiments, these file formats/structures can be accessed to obtain data used in performing the functionality described herein.

Molecular Structures

Embodiments determine molecular structures of the material being analyzed, i.e., the material for which birefringence is being calculated. Determining the molecular structures may include numerous functionalities.

An embodiment first builds three-dimensional (3D) atomistic structures, i.e., models, of the involved compounds, i.e., the compounds forming the material. Amongst other examples, such functionality may be implemented at step 101 of the method 100. In turn, an embodiment performs a conformational search for each compound. Performing a conformational search is relevant for considering molecular anisotropy and determining aspect ratios, which is used, in an embodiment, when calculating the refractive index based on an extension of the Clausius-Mossotti equation (see, e.g. J. Chem. Phys. 123, 134904, 2005). FIG. 2 illustrates an example atomistic structure 220 built according to an embodiment. The structure 220 illustrates an example structure obtained from conformational search and measurements 221a and 221b for determining the aspect ratio.

Embodiments may carry out conformational search using one or a combination of techniques. For instance, an embodiment may implement a systematic conformational search to identify conformer(s) of each compound. Alternately, conformational sampling using molecular dynamic (MD) simulations can be performed. Additional properties can be obtained from MD simulations as well. Further details regarding said properties are described hereinbelow. If MD simulations are used for conformational sampling, the final trajectory is analyzed. This includes selecting and geometrically optimizing individual molecules. A statistical analysis may be performed to determine how many molecules have the same conformation, e.g., lie within a certain energy range. This information may be used for weighting the importance of different conformations. A third possibility for conformational searching is a user generating sufficiently different distinct conformations manually. After performing the conformational search, an embodiment selects low, medium, and high-energy conformers of each compound.

After the conformational searching, the structures are aligned along one direction. Such an embodiment creates structures with ideal alignment along the molecule axis. The structures can be aligned using 3D molecular modeling visualization software. In an example embodiment, BIOVIA® Materials Studio® functionalities are used for the alignment procedure: (i) left to right, (ii) vertical, and (iii) YZ plane. The foregoing alignment procedure is one example procedure amongst other possible procedures that may be used in embodiments. Alignment procedures used in embodiments may treat models consistently and choose the correct diagonal elements of the polarizability tensors for calculating the ordinary and extraordinary refractive indices.

Figure 3:
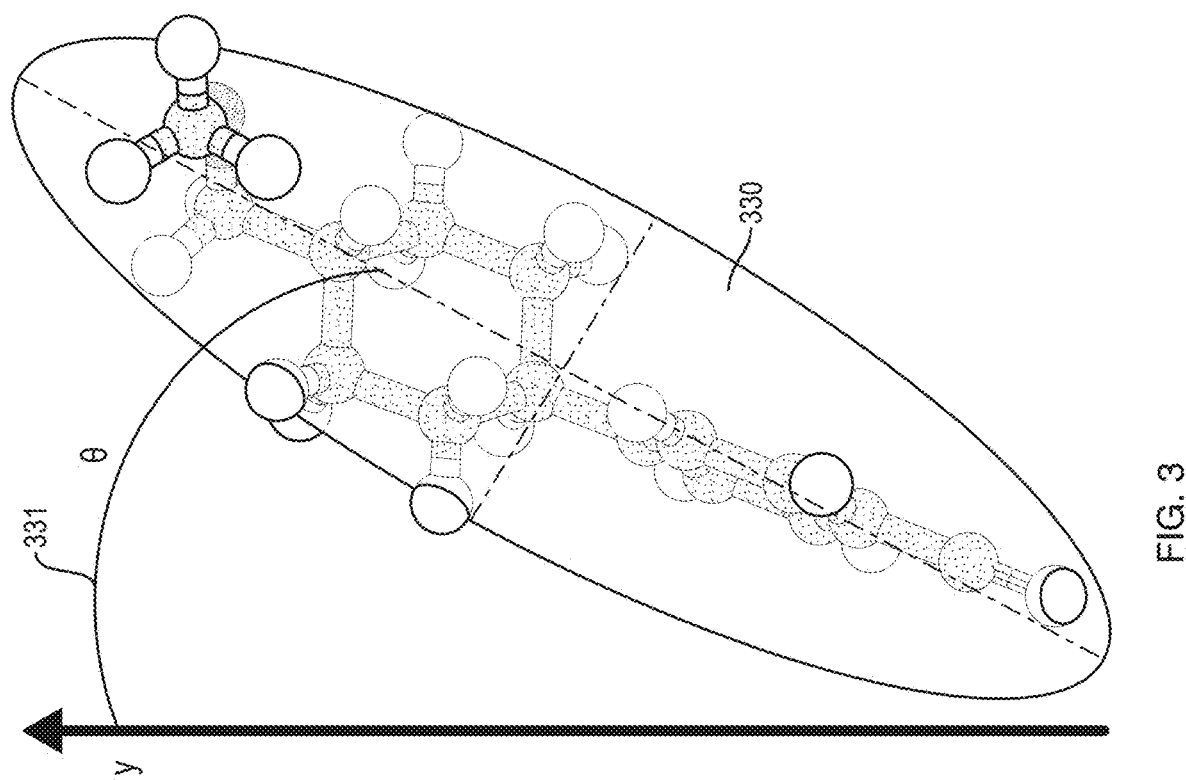
FIG. 3 depicts a tilt angle that may be computed by embodiments.

In order to take disorder and temperature effects into account, an embodiment creates additional structures with tilted orientations. According to an embodiment, the tilt angle in these additional structures is relevant for calculating the order parameter used when using, e.g., the NBJ equation (see, e.g. J. Chem. Phys. 123, 134904, 2005), for calculating the refractive index. If the tilt angle is not known, an embodiment systematically varies the tilt angle. In another embodiment, the tilt angle(s) are determined based on MD simulations as described below. FIG. 3 illustrates an example tilt angle 331 determined for the compound 330 according to an embodiment.

Calculating the Polarizability Tensor

After creating the structures, performing the conformational searching, aligning the structures, and determining the tilt angles, embodiments continue by calculating the polarizability tensor.

Calculating the polarizability tensor begins by performing geometry optimization of each structure. The geometry optimization may utilize density functional theory methods or other ab initio methods known in the art, as implemented in Turbomole, DMol3, or other such software platforms known in the art. Embodiments may also perform vibrational frequency calculations to confirm local minimum geometry.

After geometrically optimizing each structure, an embodiment calculates the molecular polarizability tensor and selects the relevant components of the polarizability tensor to calculate the ordinary and extraordinary refractive index along the molecular axis, e.g., using the Lorentz-Lorenz equation (e.g. J. Chem. Phys. 123, 134904, 2005) or using the NBJ equation (J. Chem. Phys. 123, 134904, 2005).

The Lorentz-Lorenz equation is given by:

$$\frac{n_{ij}^2 - 1}{n_{ij}^2 + 2} = \frac{\rho N_A \alpha_{ij}}{3M\varepsilon_0}$$

where n is the refractive index, $\rho$ is density, $N_A$ is Avogadro number, $\alpha$ is molecular polarizability, M is relative molar mass, $\varepsilon_0$ is vacuum permittivity, and i,j is x,y,z axis in Cartesian coordinate system.

The foregoing Lorentz-Lorenz equation can be transformed into:

$$n_{ij} = \sqrt{(2C(\alpha_{ij}) + 1)/(1 - C(\alpha_{ij}))}$$

with $$C(\alpha_{ij}) = \frac{\rho N_A \alpha_{ij}}{3M\varepsilon_0}$$

$\alpha_{ij}$ can be obtained from the polarizability tensor (alignment along y-direction):

$$\alpha_e = \alpha_{yy} \text{ and } \alpha_o = \frac{\alpha_{xx} + \alpha_{zz}}{2}$$

For the Lorentz-Lorenz equation, the density needs to be known. In embodiments, the density can be taken either from literature or calculated using molecular dynamics simulations implemented using software platforms, e.g., with Forcite, the molecular dynamics engine in BIOVIA® Materials Studio®, described further below. Other molecular dynamics simulation engines or software are suitable.

Once the extraordinary and ordinary refractive index have been calculated, if there are multiple conformations and orientations, the extraordinary and ordinary refractive indices for each of the conformations and orientations are averaged. In the case of a mixture, contributions are weighted in accordance with composition of the mixture. Further, when applying the NBJ approach, an embodiment determines the aspect ratio. Embodiments can employ different techniques to estimate the aspect ratio. One such embodiment manually determines the aspect ratio by measuring the molecular dimensions of the rigid part of the molecule along the molecular axis and perpendicular to it. Another embodiment determines the aspect ratio by defining motion groups in Materials Studio®, or other such simulation software, and determining dimensions of these motion groups. Another embodiment involves molecular dynamics simulations of a nematic phase structure of the material. Motion groups are assigned to the individual molecules of the bulk structure. Geometry optimization followed by molecular dynamics simulation at one or more temperatures are performed to equilibrate the bulk model. The dimensions of the motion groups are then analyzed. The analysis can involve averaging over simulation time and/or averaging over conformations.

After determining the aspect ratio(s) the birefringence is determined.

Determining Aspect Ratios, Density, and Tilt Angle from MD Simulations

As described above, embodiments may perform MD simulations to determine properties of the material being analyzed. Amongst other examples, these MD simulations may be used to determine tilt angles and aspect ratios.

In an embodiment, performing the MD simulations begins by building a nematic phase of a pure compound or mixture using computer simulation software. An example embodiment utilizes BIOVIA® Materials Studio® functionalities to build the nematic phase, e.g., a model of the material in a nematic phase.

According to an embodiment, building the nematic phase includes building molecular structures of component(s), i.e., compounds, of the material. Next, a Mesogen group is defined for each component, and if existing, the rigid core of the molecule is selected. In turn, motion groups are created and assigned for determining aspect ratio and subsets for each component are defined. Then, the computer simulation software, e.g., BIOVIA® Materials Studio® Amorphous Cell, builds the nematic phase using the structures with the defined Mesogen group and created/assigned motion groups. FIG. 4 is a snapshot of a molecular dynamics simulation showing a nematic phase 440 of a material.

The built nematic phase is then equilibrated at temperature(s) of interest using simulation software, e.g. Materials Studio® Forcite. Then, equilibration simulations are performed in the NVT (i.e., the number of simulated particles (N), the cell volume of the simulation cell (V), and temperature (T) are kept fixed during the simulation) and NPT (i.e., the number of simulated particles (N), the pressure (P) and temperature (T) are kept fixed during the simulation) ensemble. In turn, embodiments analyze trajectories and properties of the equilibrated structures. According to an embodiment, this analysis includes evaluating density after NPT equilibration. In an embodiment, this is directly accessible through analysis functionalities available through the computer-based simulation software used to the perform the MD simulations, e.g., Materials Studio®.

In an example embodiment, if MD simulation is used for conformational sampling, an embodiment proceeds as described hereinabove by: (i) picking individual molecules, (ii) geometrically optimizing conformers, (iii) defining energy ranges for each molecular species, (iv) assigning each geometry optimized conformer to an energy bin, (v) performing histogram analysis, i.e. count number of conformers in each bin, (vi) using this information for weighting importance of the conformation, and (vii) selecting conformations for calculating the polarizability tensor.

Such an MD simulation based embodiment then determines tilt angle for each species by averaging over time and number of molecules. In software used to perform the MD simulations, e.g., Materials Studio®, distance monitors can be defined. These defined distance monitors can be used to calculate the angle between molecule axis and room axis, i.e. the tilt angle 331 as shown in FIG. 3. The determined tilt angles may be averaged over time. In addition, a histogram or a tilt angle distribution may be generated. This information can be used to identify prevalent tilt angles, if more than one tilt angle exists. Furthermore, the distribution may be used to weight the importance of different tilt angles, if more than one tilt angle is used.

It is noted that in embodiments, experimental data can be used instead of, or in addition to, calculated properties, e.g., density. Further, machine learning-based models may be developed to predict rigid parts of the molecules, density, and/or other relevant properties needed for calculating the extraordinary and ordinary refractive indices.

Advantages

Embodiments provide a method for predicting birefringence for pure and mixed organic liquid crystals. Unlike existing approaches, described herein, that rely on an experienced guess or experimental data (which often cannot be obtained for non-pure compounds), embodiments provide a method to automatically determine birefringence. Further, existing methods are limited to select pure compounds and embodiments have no such limitations. Embodiments provide an automatic workflow that can predict polarizability, optical properties, e.g., birefringence, of liquid materials, and related compounds. Amongst other examples, the birefringence determined by embodiments can be used for virtual reality and displays of electronic devices.

Embodiments can account for temperature and disorder effects, as well as intermolecular influences, in mixtures. Minimal user input is needed. No experimental data is required (although experimental data can be incorporated to improve accuracy). Embodiments can be fully automated and, thus, greatly improve the user experience. Embodiments offer an efficient method for fast and rational exploration of product design parameters in particular, but not limited to liquid display materials. Embodiments can also be used in other workflows and on existing computer-based design and computer-based engineering applications and platforms.

Embodiments provide a technically novel and non-routine solution derived from computer technology that produces better predictions of properties of real world materials. Resulting in improvement to time/cost to manufacture.

Designers of materials often expect materials to have specific material properties for certain use cases or user applications. An Edisonian approach to materials design often results in non-optimal choices, leading to longer development cycles and wasted resources. In contrast, embodiments can be used in a computer simulation of key material properties to identify better suited materials for the desired user application from a pool of candidate materials. The better materials can be presented to a user, e.g., materials designer.

In some examples, embodiments identify virtual implements (i.e., data from simulations or modeling), at least in part, using a methodology to predict the optical properties of a material or mixtures of materials. A non-limiting example embodiment uses information from first principles methods that are encapsulated in various components to provide explicit instructions for the simulation of the desired materials property, e.g., the refractive index of the material. Advantageously, embodiments can be (i) fully based on first principles simulation techniques, (ii) applied in the absence of experimental data, and (iii) automated.

An embodiment can optimize selection of a material for real-world applications, e.g., use as a phone display and, in this way, embodiments can improve the real-world phone display and manufacturing thereof. For instance, a user designing a new phone may identify three candidate materials for the phone display, where the candidate materials have properties that meet manufacturing requirements, e.g., are easier to manipulate in the manufacturing process compared to existing materials. However, such a user may not know if the candidate materials have properties that meet display performance requirements. Embodiments solve this problem by determining the birefringence of each of these materials. In turn, a given material is selected that meets display performance requirements and the selected material is used in manufacturing the phone. In this way, a material is selected that both improves the display performance and manufacturability.

Computer Support

Embodiments can be fully automated, e.g. as Python script. Further, embodiments can be implemented in existing software and computer-aided design and computer-aided engineering platforms. For instance, embodiments can be implemented using features and functionalities of 3DS BIO-VIA® software.

Figure 5:
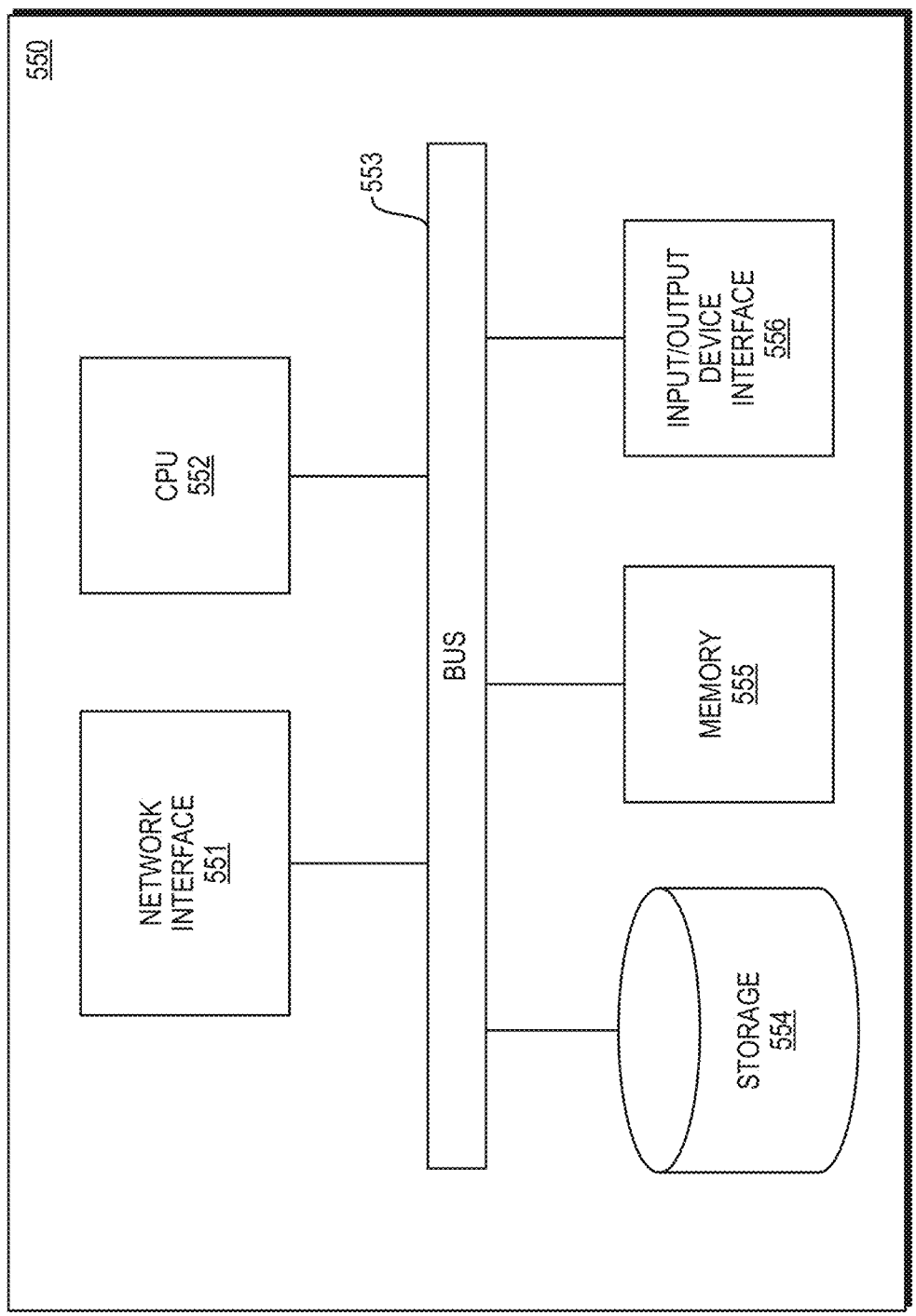
FIG. 5 is a simplified block diagram of a computer system for calculating birefringence of a material according to an embodiment.

FIG. 5 is a simplified block diagram of a computer-based system 550 that may be used to calculate birefringence of a material according to any variety of the embodiments of the present invention described herein. The system 550 comprises a bus 553. The bus 553 serves as an interconnect between the various components of the system 550. Connected to the bus 553 is an input/output device interface 556 for connecting various input and output devices such as a keyboard, mouse, touch screen, display, speakers, etc. to the system 550. A central processing unit (CPU) 552 is connected to the bus 553 and provides for the execution of computer instructions. Memory 555 provides volatile storage for data used for carrying out computer instructions. Storage 554 provides non-volatile storage for software instructions, such as an operating system (not shown). The system 550 also comprises a network interface 551 for connecting to any variety of networks known in the art, including wide area networks (WANs) and local area networks (LANs).

It should be understood that the example embodiments described herein may be implemented in many different ways. In some instances, the various methods and machines described herein may each be implemented by a physical, virtual, or hybrid general purpose computer, such as the computer system 550, or a computer network environment such as the computer environment 660, described herein below in relation to FIG. 6. The computer system 550 may be transformed into the machines that execute the methods described herein, for example, by loading software instructions implementing method 100 into either memory 555 or non-volatile storage 554 for execution by the CPU 552. One of ordinary skill in the art should further understand that the system 550 and its various components may be configured to carry out any embodiments or combination of embodiments described herein. Further, the system 550 may implement the various embodiments described herein utilizing any combination of hardware, software, and firmware modules operatively coupled, internally, or externally, to the system 550.

Figure 6:
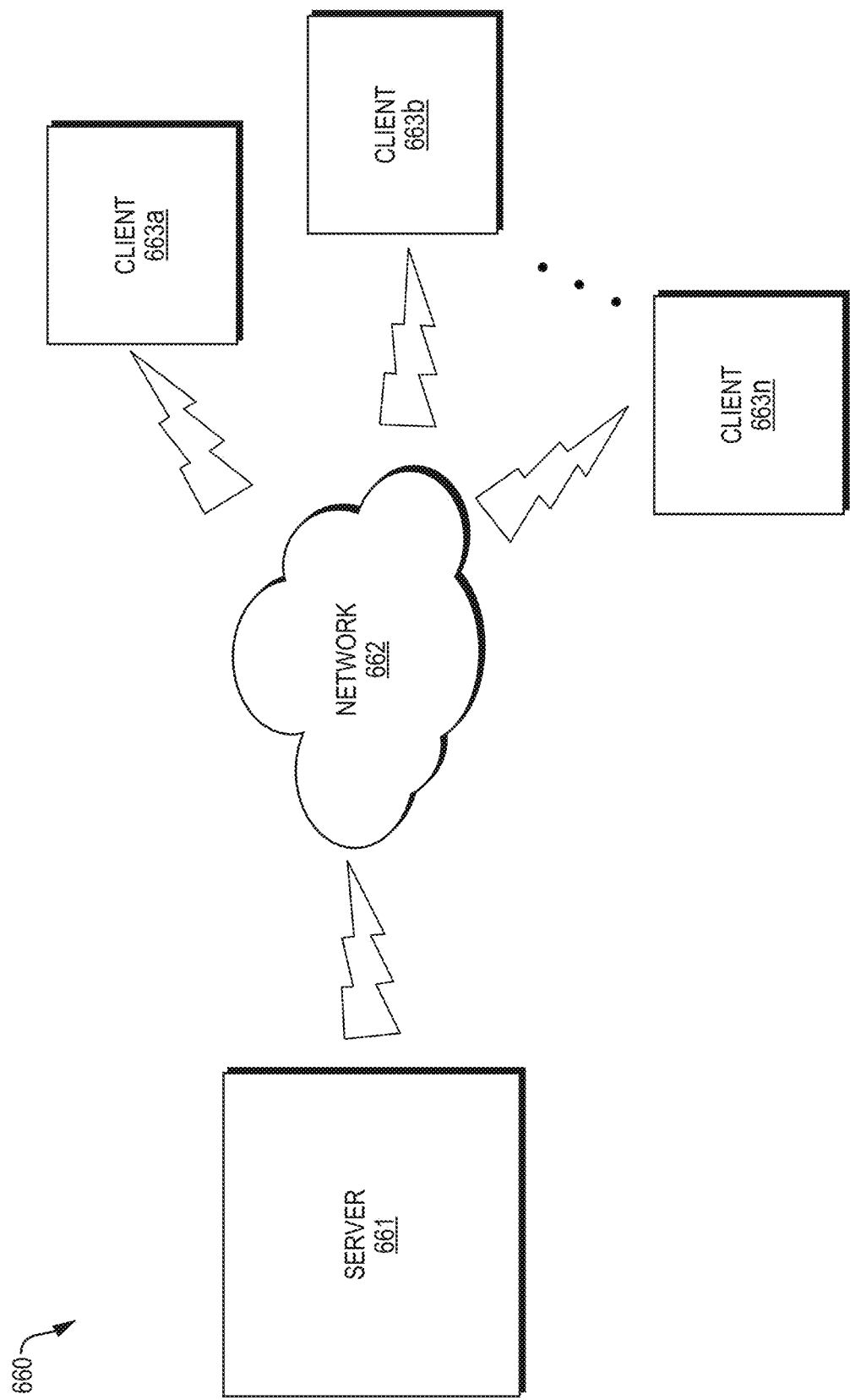
FIG. 6 is a simplified block diagram of a computer network environment in which embodiments of the present invention may be implemented.

FIG. 6 illustrates a computer network environment 660 in which embodiments of the present invention may be implemented. In the computer network environment 660, the server 661 is linked through the communications network 662 to the clients 663a-n. The environment 660 may be used to allow the clients 663a-n, alone or in combination with the server 661, to execute any of the embodiments described herein. For non-limiting example, computer network environment 660 provides cloud computing embodiments, software as a service (SAAS) embodiments, and the like.

Embodiments or aspects thereof may be implemented in the form of hardware, firmware, or software. If implemented in software, the software may be stored on any non-transient computer readable medium that is configured to enable a processor to load the software or subsets of instructions thereof. The processor then executes the instructions and is configured to operate or cause an apparatus to operate in a manner as described herein.

Further, firmware, software, routines, or instructions may be described herein as performing certain actions and/or functions of the data processors. However, it should be appreciated that such descriptions contained herein are merely for convenience and that such actions in fact result from computing devices, processors, controllers, or other devices executing the firmware, software, routines, instructions, etc.

It should be understood that the flow diagrams, block diagrams, and network diagrams may include more or fewer elements, be arranged differently, or be represented differently. But it further should be understood that certain implementations may dictate the block and network diagrams and the number of block and network diagrams illustrating the execution of the embodiments be implemented in a particular way.

Accordingly, further embodiments may also be implemented in a variety of computer architectures, physical, virtual, cloud computers, and/or some combination thereof, and thus, the data processors described herein are intended for purposes of illustration only and not as a limitation of the embodiments.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A computer-implemented method for calculating birefringence of a material, the method comprising:
building one or more three-dimensional structure models of one or more compounds forming a material;
for each of the built one or more three-dimensional structure models:
aligning the three-dimensional structure model along a molecular axis;
setting one or more tilt angles for the aligned three-dimensional structure model; and
using the aligned three-dimensional structure model with the set one or more tilt angles, calculating a molecular polarizability tensor for the aligned three-dimensional structure model with the set one or more tilt angles; and
based on the calculated molecular polarizability tensors, calculating birefringence of the material.

2. The method of claim 1 wherein the material is a liquid crystal mixture, an organic molecule-based material, an organic-molecule-based pure compound, or a mixture of organic molecules.

3. The method of claim 1 wherein building the one or more three-dimensional structure models of the one or more compounds comprises:
building one or more initial three-dimensional structure models of the one or more compounds forming the material;
based on the built one or more initial three-dimensional structure models, performing a conformational search to generate a respective set of three-dimensional structure models of conformers for each of the one or more compounds;

for each generated set of three-dimensional structure models of conformers, selecting a subset of conformers from the generated set of three-dimensional structure models of conformers; and setting (i) the one or more initial three-dimensional structure models and (ii) three-dimensional structure models of conformers corresponding to each selected subset of conformers, as the built one or more three-dimensional structure models of the one or more compounds forming the material.

4. The method of claim 3 wherein selecting a subset of conformers comprises:

selecting a low-energy conformer, a medium-energy conformer, and a high-energy conformer.

5. The method of claim 3 wherein performing a conformational search comprises at least one of:

performing a systematic conformational search;
performing a molecular dynamics simulation for conformational sampling; and
receiving user input selecting one or more desired conformers.

6. The method of claim 5 wherein performing a molecular dynamics simulation for conformational sampling comprises:

building a three-dimensional bulk structure model of the material;
using the three-dimensional bulk structure model built, performing a molecular dynamics simulation at one or more temperatures to create a trajectory;
for each of the one or more compounds, selecting from the trajectory, individual molecules of the one or more compounds;
determining a respective energy of each individual molecule selected based on a geometry optimization of the individual molecules selected;
statistically analyzing the determined respective energy of each individual molecule to define an energy range for each of the one or more compounds;
splitting up each defined energy range of the one or more compounds into sub-range bins;
assigning each conformer in each respective set of three-dimensional structure models of conformers of the one or more compounds to a given energy bin of the sub-range bins;
determining a number of conformers in each sub-range bin;
based on the determined number of conformers in each sub-range bin, identifying each selected subset of conformers and weighting importance of each conformer in each selected subset of conformers.

7. The method of claim 1 wherein setting the one or more tilt angles comprises at least one of:

systematically varying the one or more tilt angles; and
automatically determining the one or more tilt angles from a molecular dynamics simulation.

8. The method of claim 1 wherein calculating a molecular polarizability tensor using the aligned three-dimensional structure model with the set one or more tilt angles comprises at least one of:

performing geometry optimization of the aligned three-dimensional structure model with the set one or more tilt angles; and
performing vibrational frequency analysis to confirm local minimum geometry of the aligned three-dimensional structure model with the set one or more tilt angles.

9. The method of claim 1 wherein calculating birefringence of the material based on the calculated molecular polarizability tensors comprises:

for each calculated molecular polarizability tensor:
selecting relevant components from the calculated molecular polarizability tensor; and
calculating an ordinary refractive index and an extraordinary refractive index using the selected relevant components; and
calculating the birefringence using the ordinary refractive index and the extraordinary refractive index calculated for each calculated molecular polarizability tensor.

10. The method of claim 9 wherein calculating the birefringence using the ordinary refractive index and the extraordinary refractive index calculated for each calculated molecular polarizability tensor comprises at least one of:

calculating the birefringence for a conformation of the one or more compounds and one tilt angle of the set one or more tilt angles;
where the one or more tilt angles comprises a plurality of tilt angles, calculating the birefringence for (i) a conformation of the one or more compounds and the plurality of tilt angles or (ii) multiple conformations of the one or more compounds and a given tilt angle of the plurality of tilt angles, or (iii) a plurality of conformations of the one or more compounds and the plurality of tilt angles;
averaging the ordinary refractive index and the extraordinary refractive index calculated for each calculated molecular polarizability tensor; and
weighting contributions of each ordinary refractive index and each extraordinary refractive index calculated.

11. The method of claim 9 further comprising:

for each of the built one or more three-dimensional structure models, determining a respective aspect ratio; and
for each calculated molecular polarizability tensor, calculating the ordinary refractive index and the extraordinary refractive index using the selected relevant components and the determined respective aspect ratio.

12. The method of claim 1 wherein setting one or more tilt angles for the aligned three-dimensional structure model comprises:

building a nematic phase structure of the material formed of the one or more compounds;
geometrically optimizing the built nematic phase structure;
performing molecular dynamics simulations of the geometrically optimized nematic phase structure equilibrated at one or more temperatures; and
determining the one or more tilt angles, between a molecule axis and room axis for each molecule, by analyzing results of performing the molecular dynamics simulations of the geometrically optimized nematic phase structure equilibrated at the one or more temperatures.

13. The method of claim 12 wherein determining the one or more tilt angle comprises:

statistically analyzing the determined one or more tilt angles to select a subset of tilt angles.

14. The method of claim 13 wherein statistically analyzing the determined one or more tilt angles comprises at least one of:

generating a tilt angle distribution for each compound contained in the nematic phase structure;
averaging each tilt angle distribution over time of the molecular dynamics simulations; and deriving weighting factors for the tilt angles, if more than one tilt angle is applied.

15. The method of claim 1 further comprising:
calculating the density of the material.

16. The method of claim 15 wherein calculating the density of the material comprises at least one of:
performing molecular dynamics simulations for the material to determine a trajectory and analyzing the trajectory; and
performing a machine learning-based analysis to predict the density of the material.

17. The method of claim 1 further comprising:
simulating the material using the determined birefringence.

18. The method of claim 17 further comprising:
based on the simulation, determining a design for a real-world object using the simulated material.

19. The method of claim 18 wherein the real-world object is an optical display, filter, film, coating, or lens.

20. The method of claim 17 further comprising:
iterating the building, aligning, setting, calculating a molecular polarizability tensor, calculating birefringence, and simulating for each of a plurality of candidate materials; and
based on results of the simulating, selecting a given material from among the candidate materials.

21. A system for calculating birefringence of a material, the system comprising:
a processor; and
a memory with computer code instructions stored thereon, the processor and the memory, with the computer code instructions, being configured to cause the system to:
build one or more three-dimensional structure models of one or more compounds forming a material;
for each of the built one or more three-dimensional structure models:
align the three-dimensional structure model along a molecular axis;
set one or more tilt angles for the aligned three-dimensional structure model; and
using the aligned three-dimensional structure model with the set one or more tilt angles, calculate a molecular polarizability tensor for the aligned three-dimensional structure model with the set one or more tilt angles; and
based on the calculated molecular polarizability tensors, calculate birefringence of the material.

22. A non-transitory computer program product for calculating birefringence of a material, the computer program product executed by a server in communication across a network with one or more clients and comprising:
a computer readable medium, the computer readable medium comprising program instructions, which, when executed by a processor, causes the processor to:
build one or more three-dimensional structure models of one or more compounds forming a material;
for each of the built one or more three-dimensional structure models:
align the three-dimensional structure model along a molecular axis;
set one or more tilt angles for the aligned three-dimensional structure model; and
using the aligned three-dimensional structure model with the set one or more tilt angles, calculate a molecular polarizability tensor for the aligned three-dimensional structure model with the set one or more tilt angles; and
based on the calculated molecular polarizability tensors, calculate birefringence of the material.

\* \* \* \* \*